United States Patent
Bhoopal et al.

(10) Patent No.: US 10,968,182 B2
(45) Date of Patent: Apr. 6, 2021

(54) PROCESS FOR THE PREPARATION OF 2-CYANOIMIDAZOLE COMPOUNDS

(71) Applicant: Adama Makhteshim Ltd., Beer-Sheva (IL)

(72) Inventors: Meka Bhoopal, Hyderabad (IN); Sura Jagadeesh, Andhra Pradesh (IN); Bijukumar Gopinathan Pillai, Ahmedabad (IN); Michael Grabarnik, Meitar (IL); Doron Mason, Otniel (IL)

(73) Assignee: Adama Makhteshim Ltd., Beer-Sheva (IL)

( * ) Notice: Subject to any disclaimer, the term of this patent is extended or adjusted under 35 U.S.C. 154(b) by 0 days.

(21) Appl. No.: 16/487,441

(22) PCT Filed: Feb. 23, 2018

(86) PCT No.: PCT/IL2018/050211
§ 371 (c)(1),
(2) Date: Aug. 21, 2019

(87) PCT Pub. No.: WO2018/154582
PCT Pub. Date: Aug. 30, 2018

(65) Prior Publication Data
US 2020/0071278 A1    Mar. 5, 2020

(30) Foreign Application Priority Data
Feb. 23, 2017    (IN) .............................. 201731006545

(51) Int. Cl.
*C07D 233/90*    (2006.01)

(52) U.S. Cl.
CPC .................. *C07D 233/90* (2013.01)

(58) Field of Classification Search
CPC .................................................. C07D 233/90
See application file for complete search history.

(56) References Cited

FOREIGN PATENT DOCUMENTS

| CN | 10242467 | * | 4/2012 |
|----|----------|---|--------|
| CN | 105130904 | * | 12/2015 |
| CN | 103936678 | | 4/2016 |
| CN | 104292166 | | 4/2016 |
| WO | WO 2018/154582 | | 8/2018 |
| WO | WO 2018/154582 A9 | | 8/2018 |

OTHER PUBLICATIONS

Yuan et al, machine translation of CN105130904, 2015, p. 1-7 (Year: 2015).*
Li et al, English machine translation of CN 102424671, p. 1-5. (Year: 2012).*
International Preliminary Report on Patentability dated Sep. 6, 2019 From the International Bureau of WIPO Re. Application No. PCT/IL2018/050211. (8 Pages).
International Search Report and the Written Opinion dated May 30, 2018 From the International Searching Authority Re. Application No. PCT/IL2018/050211. (15 Pages).
Sizova et al. "Pyrrolo[3,2-d]Pyrimidines. IV. Synthesis and Antibacterial and Antitumor Activity of 2,4,7-Substituted Pyrrolo[3.2-d]Pyrimidines", Pharmaceutical Chemistry Journal, XP055203121, 16(11): 834-838, Nov. 1, 1982. p. 834.

* cited by examiner

*Primary Examiner* — Karen Cheng

(57) ABSTRACT

It is an object of the present invention to provide a novel and advantageous process for commercially preparing of 2-cyanoimidazole compounds. More particularly, it relates to an efficient method of preparation of cyazofamid synthetic precursor by simultaneous conversion of aldoxime group to the corresponding cyano-derivative and reducing of N-oxygenated-imidazole ring to imidazole under mild conditions using reducing agent selected from the group consisting of metal salts of sulfur-containing derivatives in the presence of a polar organic solvent.

3 Claims, No Drawings

PROCESS FOR THE PREPARATION OF 2-CYANOIMIDAZOLE COMPOUNDS

RELATED APPLICATIONS

This application is a National Phase of PCT Patent Application No. PCT/IL2018/050211 having International filing date of Feb. 23, 2018, which claims the benefit of priority of Indian Patent Application No. 201731006545 filed on Feb. 23, 2017. The contents of the above applications are all incorporated by reference as if fully set forth herein in their entirety.

FIELD OF THE INVENTION

The present invention concerns an improved process for preparation of 5-(4-methylphenyl)-1H-imidazole-2-carbonitrile represented as compound of formula (I), an important intermediate for preparing the fungicide cyazofamid.

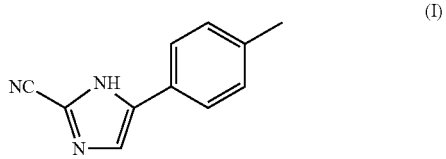

(I)

BACKGROUND OF THE INVENTION

The compound 5-(4-methylphenyl)-1H-imidazole-2-carbonitrile represented as compound of formula (I), is an important intermediate for preparing the fungicide cyazofamid. It is previously disclosed in the literature that the compound of formula (I) could be prepared by conversion of its aldoxime N-oxide precursor 1-hydroxy-4-(4-methylphenyl)-3-oxide-1H-imidazole-2-carboxaldehyde oxime represented as formula (II) to the corresponding cyano derivative and subsequent reduction of N-oxide group of the imidazole ring.

Conversion of aldoxime to the corresponding cyano-derivative using appropriate dehydrating agents such as phosphorus chloride, phosphorus pentoxide, thionyl chloride and the like have been developed and previously described in the literature. Namely, thionyl chloride is described in the literature as a common dehydration agent for conversion of aldoxime intermediate of cyazofamid to its cyano-derivative.

European patent application EP 0705823 describes the process of preparation of cyazofamid which includes the step of dehydration of aldoxime group of the intermediate represented as formula (II) using thionyl chloride in the presence of N,N-dialkylamide and further addition of sulfur chloride to produce a 2-cyanoimidazole intermediate represented as formula (I).

Japanese patent JP 2879164 describes the process of preparation of cyazofamid which includes the step of dehydration of aldoxime group of the intermediate represented as formula (II) using phosphorus or sulfur chloride or oxychloride preferably in the presence of a base to produce a 2-cyanoimidazole intermediate represented as formula (I).

Chinese patent CN 102424671 describes the process of preparation of cyazofamid which includes the step of dehydration of aldoxime group of the intermediate represented as formula (II) using thionyl chloride, and subsequent addition of a) a chlorinating agent N-chlorosuccinimide and b) of reducing agent such as sodium dithionite, sodium sulfite or sodium hydrogen sulfite to produce a 2-cyanoimidazole intermediate represented as formula (III).

The aforementioned dehydration reagents, however, have limitations in some respects such as harsh reaction conditions, long reaction time, low yields, use of toxic, expensive or less readily available reagents and tedious workup.

Thionyl chloride is a severe lachrymator which should be freshly distilled before use in chemical processes. In addition, due to its slow reaction rate and long reaction times, elevated reaction temperatures and large excess of thionyl chloride must be used to achieve a convenient rate of dehydration of aldoxime group.

The use of large excesses of thionyl chloride in dehydration reactions is undesirable, since any unreacted thionyl chloride must be removed before the product is isolated and recovered.

In addition, as already known and recited in U.S. Pat. No. 4,605,521, the use of an excess amount of thionyl chloride in combination with high reaction temperatures and long stripping times at elevated temperatures greater than 60° C. will rapidly darken organic nitriles and increase residual sulfur content which is also undesirable.

In view of the aforementioned, there is a need for an improved process for commercially preparing of 5-(p-tolyl)-1H-imidazole-2-carbonitrile represented as a compound of formula (I), an important intermediate for preparing the fungicide cyazofamid, which process is suitable for industrial use, highly efficient, low-cost, environmentally friendly, and provides a higher yield and easy workup, thereby overcoming the deficiencies of the prior art.

It has been surprisingly found that reducing agent selected from the group consisting of metal salts of sulfur-containing derivatives such as sodium metabisulfite, sodium bisulfite, sodium sulfite, potassium bisulfite, potassium metabisulfite, potassium sulfite, potassium dithionite, sodium dithionite and/or the mixtures thereof perform the successful conversion of aldoxime substituent of the imidazole ring of the compound of formula (II) to the corresponding cyano group and, at the same time reduce the oxygenated nitrogens of imidazole moiety to produce the corresponding 2-cyanoimidazole represented as formula (I). The aforementioned inventive process produces less organic waste, higher product yields and avoids the use of toxic and corrosive dehydration agents reported in prior art.

SUMMARY OF THE INVENTION

The present invention provides a process for preparation of 2-cyanoimidazole compound represented by the following formula (I):

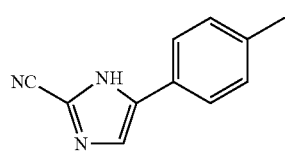

I which process comprises reacting of a compound represented by the following formula (II):

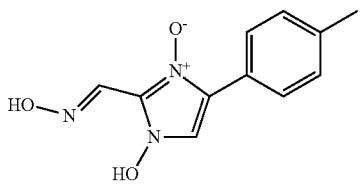

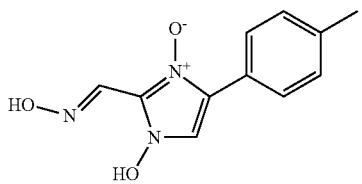

with the reducing agent selected from the group consisting of metal salts of sulfur-containing derivatives in the presence of a polar organic solvent.

Metal salts of sulfur-containing derivatives are selected from the group consisting of alkali and earth alkali metals salts and mixtures thereof; preferably from sodium metabisulfite, sodium bisulfite, sodium sulfite, potassium bisulfite, potassium metabisulfite, potassium sulfite, potassium dithionite, sodium dithionite and/or the mixtures thereof.

In another embodiment, the present invention provides a process for preparation of 4-chloro-2-cyano-imidazole compound represented by the following formula (III):

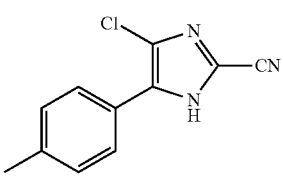

which process comprises: a) reacting of compound represented by the following formula (II):

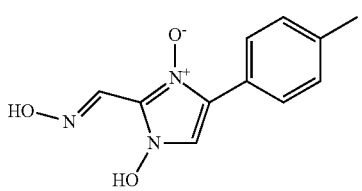

With the reducing agent selected from the group consisting of metal salts of sulfur-containing derivatives in the presence of a polar organic solvent and b) reacting the product obtained in step a) with a chlorinating agent.

In another embodiment, the present invention provides a process for the preparation of the 2-cyanoimidazole known as cyazofamid, represented by formula (IV):

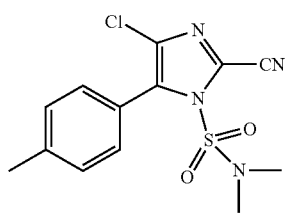

by: a) reacting of compound represented by the following formula (II):

with the reducing agent selected from the group consisting of metal salts of sulfur-containing derivatives in the presence of a polar organic solvent; b) reacting the product obtained in step a) with chlorination agent to obtain 4-chloro-2-cyano-imidazole compound of formula (III) and c) reacting the compound of formula (III) with N,N-dimethylsulfamoyl chloride in the presence of a base and a polar organic solvent.

DETAILED DESCRIPTION OF THE INVENTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one skilled in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, use of the term "about" herein specifically includes ±10% from the indicated values in the range. In addition, the endpoints of all ranges directed to the same component or property herein are inclusive of the endpoints, are independently combinable, and include all intermediate points and ranges.

Preparation of 2-cyanoimidazole Compounds

The present invention provides a process for preparation of 2-cyanoimidazole compound represented by the following formula (I):

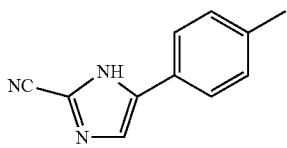

I which process comprises reacting of compound represented by the following formula (II):

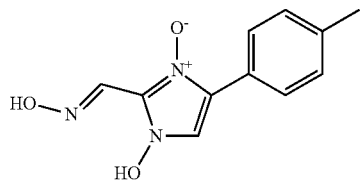

II with the reducing agent selected from the group consisting of metal salts of sulfur-containing derivatives in the presence of a polar organic solvent.

According to an embodiment, metal salts of sulfur-containing derivatives are selected from the group consisting of alkali and earth alkali metals salts and mixtures thereof; preferably from sodium metabisulfite, sodium bisulfite, sodium sulfite, potassium bisulfite, potassium metabisulfite, potassium sulfite, potassium dithionite, sodium dithionite and/or the mixtures thereof.

According to an embodiment, any polar organic solvent which has no adverse effects on the reaction can be used.

Non limiting examples of a polar organic solvent include N,N-dimethylacetamide, N,N-dimethylformamide, N-methylpyrrolidone, acetonitrile and/or the mixtures thereof.

According to an embodiment, an additional organic solvent which has no adverse effects on the reaction can be included.

Non limiting examples of such additional organic solvent include ethyl acetate, isopropyl acetate, butyl acetate and the like.

According to an embodiment, the process of preparation of compound represented as formula (I) may be carried out at a temperature of from about 40° C. to 150° C., preferably of from about 70° C. to 120° C.

According to an embodiment, the mole ratio of the compound of formula (II) to the reducing agent is from about 1:1 to 1:6, preferably from about 1:1 to about 1:3, more preferable from about 1:1 to about 1:1.5.

In another embodiment, the present invention provides a process for preparation of 4-chloro-2-cyano-imidazole compound represented by the following formula (III):

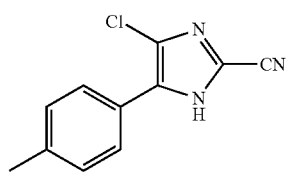

III which process comprises: a) reacting of compound represented by the following formula (II):

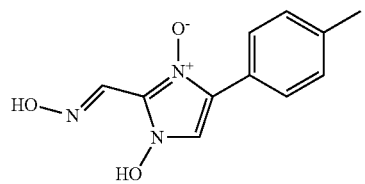

II with the reducing agent selected from the group consisting of metal salts of sulfur-containing derivatives in the presence of a polar organic solvent and b) reacting of the product of a) with chlorinating agent.

According to an embodiment, the chlorination step is carried out in the presence of a chlorination agent selected from the group consisting of but not limited to N-chlorosuccinimide, sulfuryl chloride and the like known in the art.

In an embodiment, the chlorination reaction is carried out at a temperature of from 0° C. to 40° C.

In another embodiment, the present invention provides a process for the preparation of the 2-cyanoimidazole known as cyazofamid, represented by formula (IV):

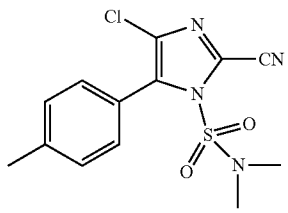

IV by: a) reacting of compound represented by the following formula (II)

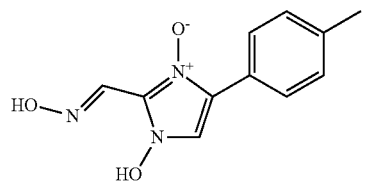

II with the reducing agent selected from the group consisting of metal salts of sulfur-containing derivatives in the presence of a polar organic solvent; b) reacting of the product formed in step a) with chlorination agent to obtain a compound of formula (III) and c) reacting the compound of formula (III) with dimethylsulfamoyl chloride in the presence of a base and a polar organic solvent.

In an embodiment, a base is preferably selected from a group consisting of alkali metal hydroxides, alkali metal carbonates, hydrides, alkaline earth metal hydroxides and alkaline earth metal carbonates. Among these, carbonates of alkali metals are preferred, and potassium carbonate is particularly preferred.

According to an embodiment, any polar organic solvent which has no adverse effects on the reaction can be used.

In a preferred embodiment, a polar organic solvent may be selected from N,N-dimethylacetamide, N,N-dimethylformamide, N-methylpyrrolidone, acetonitrile and/or the mixtures thereof.

According to an embodiment, the compound of formula (IV) known as cyazofamid is prepared in-situ without isolation of intermediates represented as formula (I) and/or of formula (III).

The progress of the reactions involved in the processes enclosed by the invention can be monitored using any suitable method, which can include, for example, chromatographic methods such as, e.g., high performance liquid chromatography (HPLC), thin layer chromatography (TLC), and the like.

In yet another embodiment, the compounds of formula (I), (III) and (IV) can be isolated from the reaction mixture by any conventional techniques well-known in the art. Such isolation techniques can be selected, without limitation, from the group consisting of concentration, extraction, precipitation, cooling, filtration, crystallization, centrifugation, and a combination thereof, followed by drying.

According to an embodiment, the resultant compound of formula (I) is present at a purity of at least 80%, at least 85%, at least 88%, at least 89%, at least 90%, at least 91%, at least 92%, at least 93%, at least 94%, at least 95%, at least 96%, at least 97%, at least 98%, or at least 99%. In particular, the use of reducing agents selected from the group consisting of metal salts of sulfur-containing derivatives instead of thionyl chloride or other corrosive dehydration agents reported in prior art, reduces the cost of production, simplifies work-up, and minimizes any toxic waste and further disposal problems.

The following examples are presented in order to illustrate certain embodiments of the invention. They should in no way, however, be construed as limiting the broad scope of the invention. One skilled in the art can readily devise many variations and modifications of the principles disclosed herein without departing from the spirit and scope of the invention.

Example 1: Preparation of (4-methylphenyl)-1H-imidazole-2-carbonitrile 250 g of 1-hydroxy-4-(4-methylphenyl)-3-oxide-1H-imidazole-2-carboxaldehyde oxime (0.95 mole) and 750 ml N,N-dimethylacetamide were mixed in a 5 liter flask and heated to 100° C. Sodium metabisulfite (235 g, 1.2 moles) was charged in portions. The mixture was held at 100° C. for 8 hours. The mixture was cooled to room temperature and 2000 ml water was added to precipitate the product. The solid was filtered off and washed with water and toluene, and dried. 139 g of crude (4-methylphenyl)-1H-imidazole-2-carbonitrile was obtained, purity 94.6%.

Example 2: Preparation of (4-methylphenyl)-1H-imidazole-2-carbonitrile 250 g of 1-hydroxy-4-(4-methylphenyl)-3-oxide-1H-imidazole-2-carboxaldehyde oxime (0.95 mole), 625 ml N,N-dimethylacetamide and 125 ml acetonitrile were mixed in a 5 liter flask and heated to 80° C. Sodium bisulfite (255 g, 2.4 moles) was charged in portions. The mixture was heated slowly to 105° C. and held for 4 hours. The mixture was cooled to room temperature and 1500 ml water was added to precipitate the product. The solid was filtered off and washed, cleaned and dried as described in Example 1, to obtain 140 g of (4-methylphenyl)-1H-imidazole-2-carbonitrile, purity 95.3%.

Example 3: Preparation of 5-chloro-4-(4-methylphenyl)-1H-imidazole-2-carbonitrile 110 g of the product from Example 1 was mixed in a 500 ml flask with 55 ml N,N-dimethylacetamide and 55 ml acetonitrile. 86 g of sulfuryl chloride was added dropwise, maintaining the temperature below 25° C. After the addition was complete the mixture was stirred for a further hour at 20° C. The reaction mass was neutralized with 10% sodium hydroxide, and stirred for a further hour. The crude product was filtered off, washed with water, re-slurried in toluene, filtered, and dried in a vacuum oven to obtain 104 g of 5-chloro-4-(4-methylphenyl)-1H-imidazole-2-carbonitrile.

Example 4: Preparation of 4-chloro-2-cyano-N,N-dimethyl-5-(4-methylphenyl)-1H-imidazole-1-sulfonamide 90 g of product from Example 3 was mixed with 117 g of potassium carbonate and 100 ml of ethyl acetate in a 500 ml flask. The mixture was heated to 75° C., and 87 g N,N-dimethylsulfamoyl chloride was added dropwise over 30 minutes. The temperature was maintained for 10 hours. After cooling, ethyl acetate and water were added, and the mixture was filtered. The solid was washed with water and with ethyl acetate, and dried to obtain 68 g of 4-chloro-2-cyano-N,N-dimethyl-5-(4-methylphenyl)-1H-imidazole-1-sulfonamide, purity 96.1%.

What is claimed is:

1. A process for preparation of 2-cyanoimidazole compound represented by the following formula (IV):

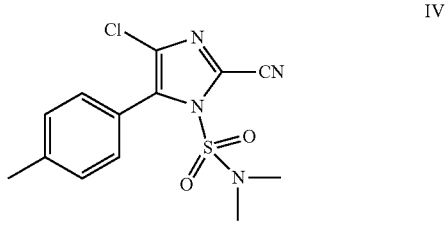

which process comprises:
a) reacting of compound represented by the following formula (II):

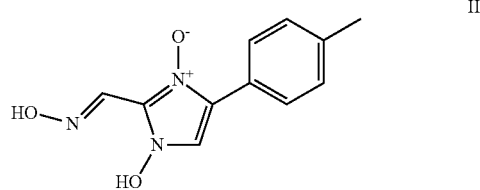 [SMILES: Cc1ccc(-c2cn(O)c(/C=N/O)[n+]2[O-])cc1]

with the reducing agent selected from the group consisting of metal salts of sulfur-containing derivatives to thereby obtain a compound of Formula I:

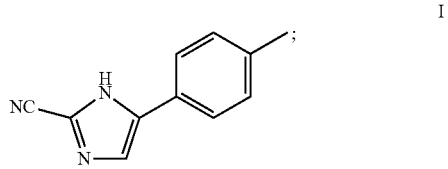

b) reacting the compound represented by Formula I with a chlorinating agent to thereby obtain a compound represented by Formula III:

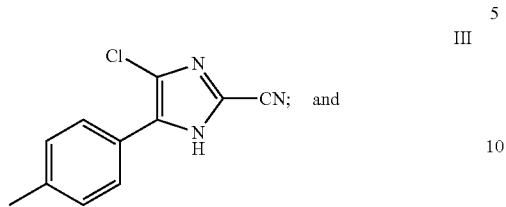

III and c) reacting the compound represented by Formula III with N,N-Dimethylsulfamoyl chloride in the presence of a base and a polar organic solvent, thereby preparing the 2-cyanoimidazole compound represented by the following formula (IV).

2. The process according to claim 1, wherein the base is selected from a group consisting of alkali metal hydroxides, alkali metal carbonates, hydrides, alkaline earth metal hydroxides and alkaline earth metal carbonates.

3. The process according to claim 1, which comprises in-situ preparation of the compound represented by formula (IV), without isolation of a compound represented as formula (I) and/or a compound represented by formula (III).

* * * * *